US008342679B2

(12) United States Patent
Seeto

(10) Patent No.: US 8,342,679 B2

(45) Date of Patent: Jan. 1, 2013

(54) METAL DETECTABLE LENS CARRIER

(75) Inventor: Donald S. Seeto, Framingham, MA (US)

(73) Assignee: 3M Innovative Properties Company, St. Paul, MN (US)

(*) Notice: Subject to any disclaimer, the term of this patent is extended or adjusted under 35 U.S.C. 154(b) by 358 days.

(21) Appl. No.: 12/764,127

(22) Filed: Apr. 21, 2010

(65) Prior Publication Data

US 2011/0261313 A1 Oct. 27, 2011

(51) Int. Cl.
*G02C 1/00* (2006.01)

(52) U.S. Cl. .......................................... 351/41; 351/51

(58) Field of Classification Search .................. 351/158, 351/41, 102, 104, 51, 52; 264/40.5, 2.2, 264/2.3, 328.88, 334; 428/8.08, 323, 426; 425/139, 556, 572

See application file for complete search history.

(56) References Cited

U.S. PATENT DOCUMENTS 2,981,022 A * 4/1961 Anger, Jr. ...................... 351/51
3,923,946 A 12/1975 Meyer
3,962,505 A 6/1976 Avery
4,024,318 A 5/1977 Forster et al.
4,045,125 A 8/1977 Farges
4,071,293 A 1/1978 Avery
4,222,640 A 9/1980 Bononi
4,632,527 A 12/1986 Masso et al.
5,018,223 A 5/1991 Dawson et al.
5,023,597 A 6/1991 Salisbury
5,164,707 A 11/1992 Rasmussen et al.
5,165,992 A 11/1992 Yajima
5,991,072 A 11/1999 Solyntjes et al.
6,040,053 A 3/2000 Scholz et al.
6,104,534 A 8/2000 Ohta
6,113,482 A 9/2000 Licata
6,168,273 B1 1/2001 Dupraz et al.
6,177,113 B1 1/2001 Kress et al.
6,327,087 B1 12/2001 Hashimoto et al.
6,577,358 B1 6/2003 Arakawa et al.
6,783,238 B1 8/2004 Stepper
6,853,492 B1 2/2005 Lau et al.
6,863,397 B2 3/2005 Nakano
7,241,006 B2 7/2007 Zelman
7,294,405 B2 11/2007 Richter et al.
7,390,580 B1 6/2008 Dupont
7,967,435 B1 6/2011 Seeto
2004/0211653 A1 10/2004 Aisenbrey
2005/0229938 A1 10/2005 Jenkins, Jr.
2007/0298242 A1 12/2007 Huo
2009/0213322 A1 8/2009 Urabe et al.

FOREIGN PATENT DOCUMENTS

CN 200947139 Y 9/2007
EP 0 187 304 7/1986
EP 2 103 978 9/2009
GB 1261242 1/1972
GB 2315698 A 1/1998
WO WO 98/26327 6/1998
WO WO 00/00855 1/2000
WO WO 2007/012898 A1 2/2007

OTHER PUBLICATIONS

El-Hiti, et al., "Electrical Properties of Thin Chromium Films," Journal of Materials Science Letters 8, (1989), pp. 329-333.

* cited by examiner

*Primary Examiner* — Hung Dang

(57) ABSTRACT

A metal detectable lens carrier that includes a polymeric material and metal particulate dispersed throughout the polymeric material. The metal detectable lens carrier is configured to hold one or more lenses. Eyewear including such lens carriers and methods of detecting thereof are also disclosed.

20 Claims, 4 Drawing Sheets

100
102
104

Provide Metal Detectable Safety Eyewear — 62
Pass at Least a Portion of the Lens Carrier Through a Metal Detector — 64
Detect at Least the Portion of the Lens Carrier — 66

METAL DETECTABLE LENS CARRIER

FIELD

The present disclosure relates to lens carriers that may be detectable by a metal detector.

BACKGROUND

Automated machinery utilized in various industries, including the food industry, can cause chips or slivers of metal to be generated. To prevent such contamination, metal detectors are utilized to monitor such processes. A typically utilized metal detector generates two magnetic fields and has a transducer in the middle. A converter compares the two magnetic fields to sense variations in the field. A variation in the field indicates that metal is within the detection area.

Workers in the food industry usually wear safety eyewear in order to protect them from various contaminants entering the eyes. If commonly utilized safety eyewear is dropped into food processing machinery, it can be crushed and can sometimes be almost undetectable by the naked eye. For at least that reason, it would be beneficial if safety eyewear or portions of safety eyewear could be detectable under such circumstances.

BRIEF SUMMARY

Disclosed herein is a metal detectable lens carrier that includes a polymeric material and metal particulate dispersed throughout the polymeric material. The metal detectable lens carrier is configured to hold one or more safety lenses.

Also disclosed is metal detectable eyewear that includes at least one optical lens and a lens carrier configured to hold the at least one optical lens. The lens carrier includes polymeric material and metal particulate dispersed throughout the polymeric material.

Also disclosed is a method of detecting at least a portion of a metal detectable safety eyewear, the metal detectable eyewear including at least one optical lens and a lens carrier configured to hold the at least one optical lens, wherein the lens carrier includes polymeric material and metal particulate dispersed throughout the polymeric material The method further includes passing at least a portion of the lens carrier through a metal detector, and detecting the at least a portion of the metal detectable safety eyewear by detecting the metal particles in the lens carrier through use of a metal detector.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying drawing that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Figure 1:
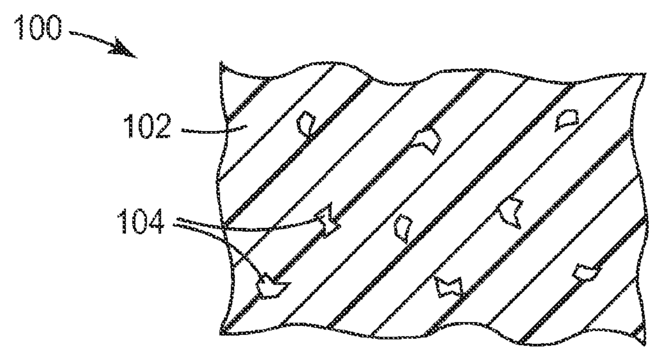
FIG. 1 shows schematically a portion of a metal detectable lens carrier.
Figure 2:
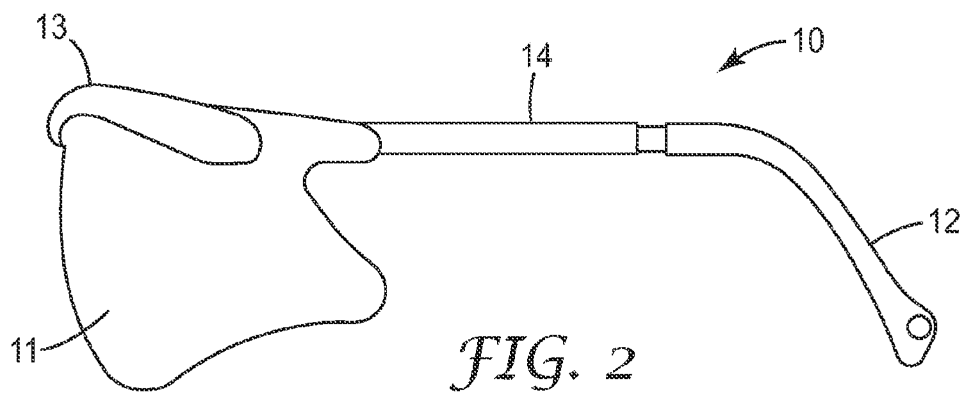
FIG. 2 depicts a lens carrier that may be used in glasses.

Disclosed herein are metal detectable lens carriers, such as metal detectable eyewear lens carriers that may be used in safety eyewear or other eyewear, prescription or plano. Exemplary embodiments of the present disclosure may be advantageously detectable by the same equipment that is already in place to detect metal fragments in food processing areas. Generally, metal detectable lens carriers include any structure or structures that can be configured to hold at least one lens to be worn by a user. Disclosed metal detectable lens carriers generally include a polymeric material and metal particulate. As illustrated in FIG. 1, which shows a portion of a metal detectable lens carrier 100, the metal particulate 104 can generally be dispersed in the polymeric material 102.

Polymeric materials that can be used to make metal detectable safety lens carriers can include one or more polymers. In embodiments, thermoplastic polymers can be utilized. Polymers that can be utilized include relatively hard, rigid materials. Exemplary polymeric materials include for example polyamides, polyolefins, polycarbonates, vinyl polymers, polyethers, and copolymers thereof (for example thermoplastic elastomers). Examples of polyamides include for example nylon-6, nylon-6,6 and nylon-6/6,6 copolymers, nylon-11, nylon-12 and blends of such polyamides. Examples of polyolefins include for example polyethylene, polystyrenes, and polypropylene, and copolymers including such polymers such as acrylonitrile butadiene styrene copolymer. Examples of polycarbonates include for example polycarbonate, and poly bisphenol A. Examples of vinyl polymers include polyvinyl chloride (PVC). Examples of polyethers include polyoxymethylene (POM). In embodiments, metal detectable safety lens carriers can be made of a polyamide, for example nylon, for example nylon 6-6.

Metal detectable lens carriers can also include one or more types of metal particulates 104 dispersed throughout the polymeric material 102. Particulates 104 can include particles, fibers, or whiskers. Preferably, the metal particulate includes a plurality of fibers (e.g., 104), such as metal fibers, dispersed throughout the polymeric material 102. Although suitable fibers typically have a length that is greater than a thickness, often the fibers are not regularly shaped. For example, cross-sections of such fibers may not be uniform in shape (in some exemplary embodiments a typical fiber cross-section would resemble a section of a cotton ball). Some exemplary embodiments may have typical sizes of fiber cross-section diameters of about 10 to 300 microns, and more typically of about 20 to 50 microns. Typical lengths of the fibers may be 1 cm or less, 5 mm or less, or 3 mm or less. However, other dimensions are within the scope of the present disclosure. Furthermore, fiber shapes can change during processing. For example, during extrusion process a fiber that is initially stretched out lengthwise may assume a configuration resembling the shape of a U or a more complex configuration. Particulates that are not clearly classified as fibers may nonetheless have sizes similar to those mentioned in connection with fibers. In some exemplary embodiments, particulates may have an average diameter of about 1 to 300 microns.

The metal particulates can include any material that is detectable by a metal detector. The metal particulates can include elements, compounds, or alloys. Generally, such materials are either ferrous, conductive, or both. In some embodiments, the metal particulates can include, for example, iron containing metals such as iron, steel and/or stainless steel. In further embodiments, the metal particulates can include for example conductive metals such as silver (Ag), copper (Cu), gold (Au), aluminum (Al), beryllium (Be), iridium (Ir), tungsten (W), molybdenum (Mo), cobalt (Co), zinc (Zn), nickel (Ni), chromium (Cr), titanium (Ti), carbon black, and graphite.

The amount of polymeric material 102 and metal particulates 104 are chosen so that the particulate dispersion within the polymeric material has desired properties. For example, the amount of polymer and metal particulates can be chosen based at least in part on the desired level of detectability, desired physical properties of the polymeric material (for example strength, shatter resistance, etc.), desired ability to process the polymeric material into lens carrier forms, or some combination thereof. As the amount of metal particulate is increased (relative to the amount of polymer), the polymeric material will become more detectable via a metal detector, but can also become less shatter resistant, for example. This can happen because the metal particulates, if to excessive in amount, can interfere with the polymer chains and produce a brittle plastic. As the amount of polymer is increased (relative to the amount of metal particulate), the polymeric material will become less detectable via a metal detector, but can also be more shatter resistant, for example.

In exemplary embodiments, the amount of polymeric materials 102 and metal particulates 104 can be chosen based on a desired balance between the opposing properties that the two components provide. In some embodiments, the amount (by weight) of metal particulates 104 can be from about 5% to about 50% of the weight of a lens carrier portion 100 in which the particulates 104 are located or of the entire lens carrier (with the corresponding amount of the polymeric materials 102 in which the particulates are dispersed of about 95% to about 50%). In other embodiments, the amount (by weight) of metal particulates can be from about 10% to about 20% of the weight of a lens carrier portion or of the entire lens carrier (with the corresponding amount of the polymeric materials of about 90% to about 80%). In yet other embodiments, the amount (by weight) of metal particulates can be from about 12% to about 14% of the weight of a lens carrier portion or of the entire lens carrier (with the corresponding amount of the polymeric materials of about 88% to about 86%).

The polymeric material may also contain optional additives, including for example, crosslinking agents, antioxidants, processing aids, UV stabilizers, surfactants, pigments, dyes, coupling agents, plasticizers, suspending agents, flame retardants, and accelerators. The amounts of these materials can generally be selected to provide the desired properties. In some embodiments, polymeric materials can include at least UV stabilizers, and dyes for example.

The metal particulates are generally dispersed in the polymeric material. Generally, this phrase refers to the metal particulate being distributed throughout the polymeric material of at least a portion of a lens carrier according to the present disclosure (e.g., as illustrated in FIG. 1) and not being specifically limited to a particular region (for example, in embodiments of the present disclosure, the metal particulate is not in the form of a layer on the polymer and is not in the form of a wire or another macroscopic form that is disposed in a highly localized area within or on the polymeric material of a lens carrier). The metal particulate need not be homogeneously dispersed throughout the polymer, but can be relatively uniformly dispersed throughout the polymer. The metal particulate can generally be dispersed in the polymer, as would typically occur via mixing the two components together prior to solidifying the polymeric material.

The polymeric material can be formulated and processed as would be known to one of skill in the art. In embodiments, precursors of a polymer, which can be referred to as monomers or oligomers can be combined with the metal particulates, polymerized, and cured to form at least a portion of a lens carrier. In embodiments, a polymer itself can be combined with the metal particulates and cured to form at least a portion of a lens carrier. In embodiments, where a polymeric material is combined with metal particulates, solid polymeric material and metal particulates can be combined together, heated to above the melting point of the polymeric material to ensure complete mixing of the mixture and then formed into at least a portion of a lens carrier. In other embodiments where the polymeric material is combined with metal particulate, the two can be combined and injection molded to form at least a part of a lens carrier. In some exemplary embodiments, the above-referenced techniques may be used to form an entire lens carrier.

The polymeric material can be formed into any type of lens carrier or a part of a lens carrier. A lens carrier as disclosed herein can include one or more than one component that function (together in the case of more than one component) to hold one or more lenses. A lens carrier can also function to allow a user to utilize the at least one lens, for example, as eye protection. Polymeric materials as disclosed herein can be utilized to make any type of lens carrier into a metal detectable lens carrier.

Exemplary types of lens carriers according to the present disclosure may be used in various types of eyewear, such as safety eyewear, including those that are depicted in FIGS. 2, 3, 4, 5, and 6. The eyewear in FIG. 2 can be referred to as glasses. The exemplary glasses can include a lens carrier 10, which in this exemplary embodiment includes temples 12 (although two temples are typically provided in glasses, only one is shown for simplicity), a frame 13, and optional links 14 (only one is shown for simplicity). This exemplary lens carrier 10 functions to hold a single lens 11. However, such exemplary embodiments may be configured to hold more than one lens and/or may include more or fewer components. In some embodiments, all of the portions of the lens carrier 10 depicted in FIG. 2 (the temples 12, the frame 13, and optional links 14) can be made of polymeric material containing a metal particulate as disclosed herein to render each piece of the lens carrier 10 individually detectable. In other embodiments, less than all portions of the lens carrier 10 depicted in FIG. 2 can be made of polymeric material containing a metal particulate as disclosed herein. In other embodiments, only one portion of the lens carrier depicted in FIG. 2 can be made of polymeric material as disclosed herein.

Figure 3:
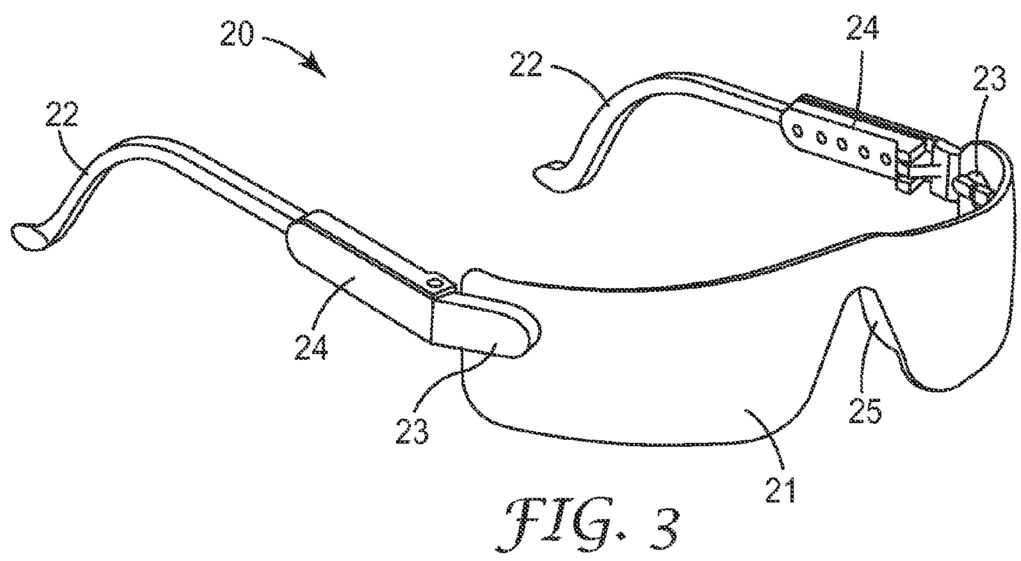
FIG. 3 depicts a lens carrier that also may be used in glasses.

The eyewear depicted in FIG. 3 can also be referred to as glasses. The exemplary glasses include a lens carrier 20, which in this exemplary embodiment includes temples 22, temple attachment portions 23, which cooperate to secure the lens 21 to the remainder of the lens carrier 20, optional links 24, and one or more, typically two, nosepieces 25. This lens carrier also functions to hold a single lens 21. However, such exemplary embodiments may be configured to hold more than one lens and/or may include more or fewer components. In some embodiments, all of the portions of the lens carrier 20 depicted in FIG. 3 (the temples 22, the frame 23, optional links 24, and the one or more nosepieces 25) can be made of polymeric material containing a metal particulate as disclosed herein to render each piece of the lens carrier 20 individually detectable. In other embodiments, less than all portions of the lens carrier depicted in FIG. 3 can be made of polymeric material containing a metal particulate as disclosed herein. In other embodiments, only one portion of the lens carrier depicted in FIG. 3 can be made of polymeric material as disclosed herein. In one embodiment, only the one or more nosepieces 25 can be made of polymeric material containing a metal particulate as disclosed herein.

Figure 4:
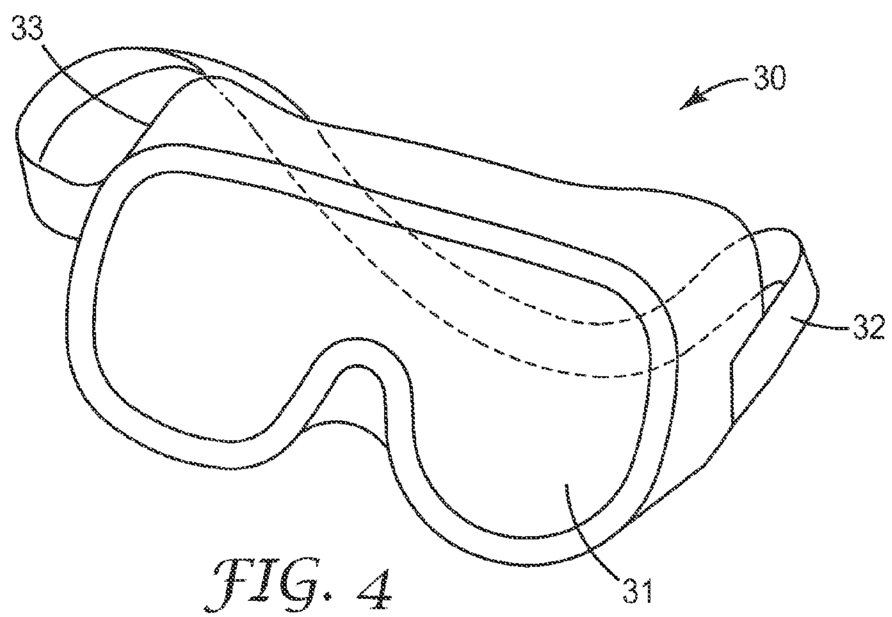
FIG. 4 depicts a lens carrier that may be used in goggles.

The exemplary eyewear depicted in FIG. 4 can be referred to as goggles. The exemplary goggles include a lens carrier 30 that includes a strap 32 and a frame 33 (which can be a single unitary piece, or can be made of more than one individual pieces formed into the exemplary frame 33). This lens carrier 30 functions to hold a single lens 31. However, such exemplary embodiments may also be configured to hold more than one lens and/or may include more or fewer components. In some embodiments, all of the portions of the lens carrier depicted in FIG. 4 (the strap 32 and the frame 33) can be made of polymeric material containing a metal particulate as disclosed herein to render each piece of the lens carrier 30 individually detectable. In other embodiments, less than all portions of the lens carrier 30 depicted in FIG. 4 can be made of polymeric material containing a metal particulate as disclosed herein. In some embodiments, only one portion of the lens carrier depicted in FIG. 4 can be made of polymeric material containing a metal particulate as disclosed herein.

Figure 5A:
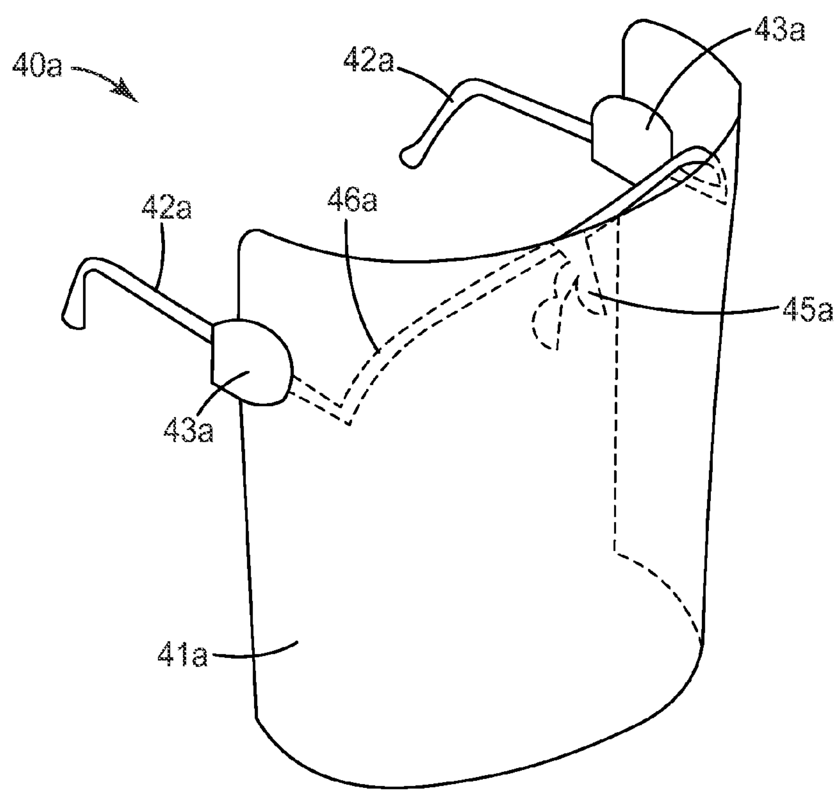
FIGS. 5A and 5B depict lens carriers that may be used in safety shields.

The eyewear depicted in FIG. 5A can be referred to as a safety shield. The exemplary safety shield includes a lens carrier 40*a*, which in this exemplary embodiment includes temples 42*a*, temple attachment portions 43*a*, which cooperate to secure the lens 41*a* to the remainder of the lens carrier 40*a*, optional internal frame 46*a*, and one or more, typically two, nosepieces 45*a*. Such exemplary embodiments may also be configured to include more or fewer components. This exemplary lens carrier also functions to hold a single lens 41*a*. In some embodiments, all of the portions of the lens carrier 40*a* depicted in FIG. 5A (the temples 42*a*, the frame 43*a*, optional internal frame 46*a*, and one or more nosepieces 45*a*) can be made of polymeric material containing a metal particulate as disclosed herein to render each piece of the lens carrier individually detectable. In other embodiments, less than all portions of the lens carrier 40*a* depicted in FIG. 5A can be made of polymeric material containing a metal particulate as disclosed herein. In some embodiments, only one portion of the lens carrier depicted in FIG. 5A can be made of polymeric material as disclosed herein. In one embodiment, only the one or more nosepieces 45*a* can be made of polymeric material containing a metal particulate as disclosed herein.

Figure 5B:
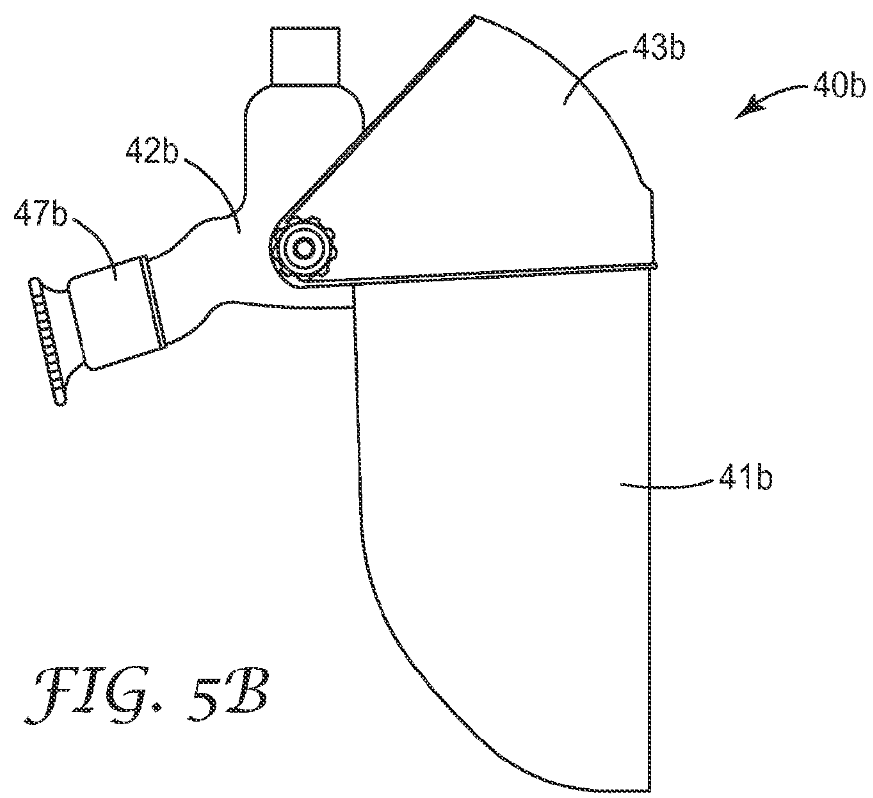

FIG. 5B depicts another exemplary safety shield. The exemplary safety shield in FIG. 5B includes a lens carrier 40*b* that includes a headband or head cradle 42*b* that may also include an adjustment device 47*b*, and a frame 43*b*. It should be noted that the frame 43*b* in a safety shield can also be referred to as a crown. Such exemplary embodiments may also be configured to include more or fewer components. This exemplary lens carrier 40*b* functions to hold a single lens 41*b*. In some embodiments, all of the portions of the lens carrier 40*b* depicted in FIG. 5B (the strap 42*b*, the adjustment device 47*b*, and the frame 43*b*) can be made of polymeric material containing a metal particulate as disclosed herein to render each piece of the lens carrier individually detectable. In other embodiments, less than all portions of the lens carrier 40*b* depicted in FIG. 5B can be made of polymeric material containing a metal particulate as disclosed herein. In some embodiments, only one portion of the lens carrier depicted in FIG. 5B can be made of polymeric material containing a metal particulate as disclosed herein.

Figure 6:
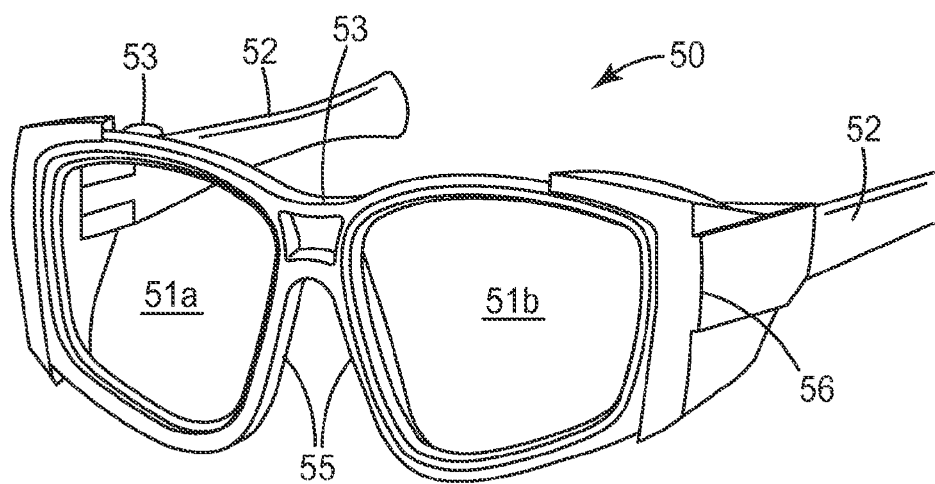
FIG. 6 depicts a lens carrier that may be used in glasses that include two lenses.
Figure 7:
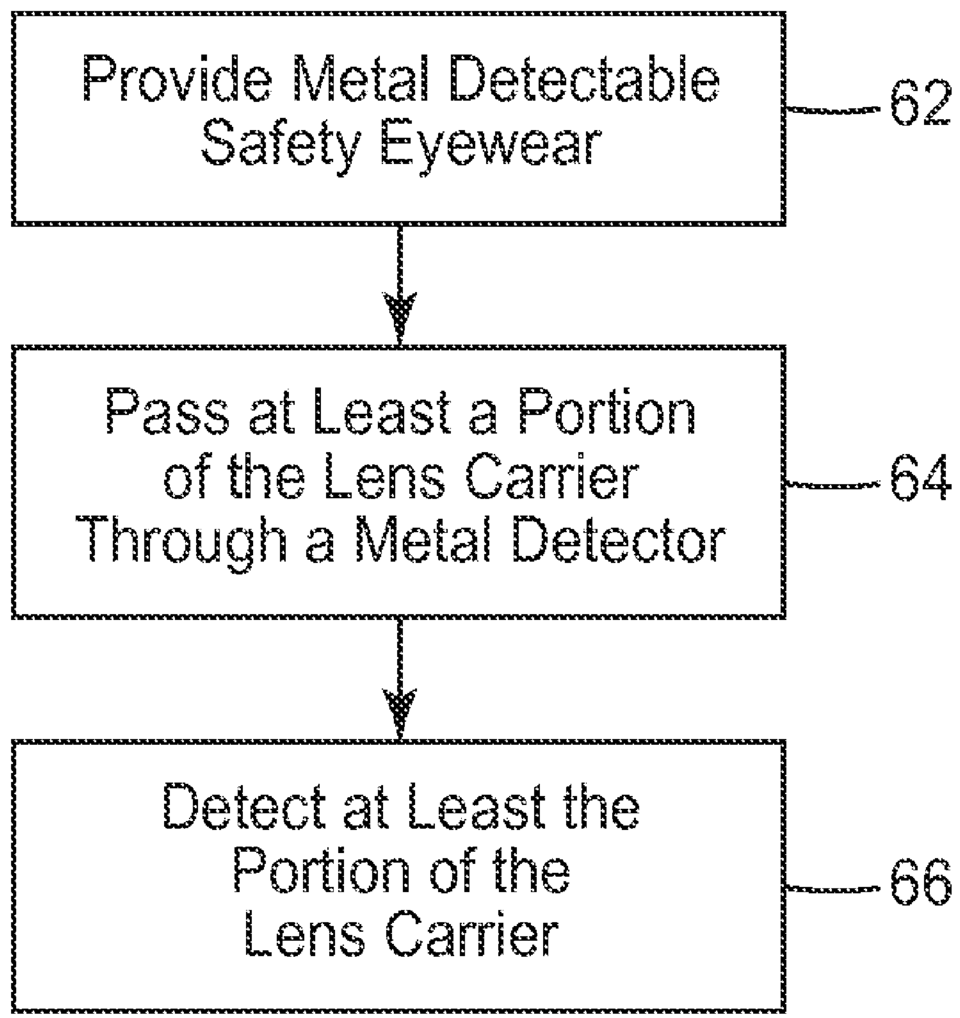
FIG. 7 is a flow chart depicting an exemplary method as disclosed herein.

The eyewear depicted in FIG. 6 can also be referred to as glasses. The exemplary glasses include a lens carrier 50 that includes temples 52, a frame 53 (the various portions of the frame 53 cooperate to secure the lenses 51*a* and 51*b*), and one or more, typically two, nosepieces 55. This lens carrier 50 functions to hold two lenses 51*a* and 51*b*. The exemplary lens carrier may also be configured to hold only one lens and/or to include more or fewer components. In some embodiments, all of the portions of the lens carrier 50 depicted in FIG. 6 (the temples 52, the frame 53, and the nosepieces 55) can be made of polymeric material containing a metal particulate as disclosed herein to render each piece of the lens carrier individually detectable. In other embodiments, less than all portions of the lens carrier depicted in FIG. 6 can be made of polymeric material containing a metal particulate as disclosed herein. In some embodiments, only one portion of the lens carrier depicted in FIG. 6 can be made of polymeric material containing a metal particulate as disclosed herein. In one embodiment, only the one or more nosepieces 55 can be made of polymeric material containing a metal particulate as disclosed herein. The exemplary glasses in FIG. 6 also include optional side shields 56. The optional side shields 56 can also be made of a polymeric material containing a metal particulate as disclosed herein, in addition to or instead of other exemplary components of the lens carrier 50.

It should also be noted that lens carriers, such as those depicted in FIGS. 2 through 6, can include components that are not depicted herein. Such optional components can be, but need not be made of polymeric material containing a metal particulate as disclosed herein, thereby rendering them independently metal detectable. In addition, such exemplary embodiments may have other suitable configurations and/or may include fewer components. The various components of the exemplary embodiments shown in FIGS. 2-6 may also be modified and interchanged as desired.

Disclosed lens carrier is expected to pass various standardized tests for safety glasses. For example, disclosed lens carriers is expected to pass industrial safety glass standards, such as for example ANSI Z87.1. For high speed impact, ANSI Z87.1 requires safety glasses to be able to resist impact from a 6.35 mm (¼ in) diameter steel ball traveling at a velocity of 45.7 meters/second (about 150 feet/second). For basic impact requirements, a 25.4 mm steel ball is dropped from a height of 127 mm (50 in) onto the lens. ANSI Z87.1 requires safety goggles to be able to resist impact from a 6.35 mm (¼ in) diameter steel ball traveling at a velocity of 76.2 meters/second (about 250 feet/second). ANSI Z87.1 requires safety shields to be able to resist impact from a 6.35 mm (¼ in) diameter steel ball traveling at a velocity of 91.4 meters/second (about 300 feet/second). Disclosed lens carriers are also expected to pass various other industrial safety glass standards that can be determined by various governmental entities or countries.

A portion of any component making up a lens carrier according to the present disclosure can be independently metal detectable. For example, if a frame (for example) from a lens carrier is fractured, any portion of that frame can be metal detectable. Disclosed lens carriers can be detected by a metal detector that is set to detect the equivalent of a 1.5 mm steel ball. In embodiments, a portion of a disclosed lens carrier can be detected by a metal detector that is set to detect the equivalent of a 1.5 mm steel ball. In embodiments, a portion of a disclosed lens carrier as small as about 0.08 g can be detected by a metal detector that is set to detect the equivalent of a 1.5 mm steel ball.

Disclosed lens carriers can be utilized in combination with one or more lenses, such as prescription or plano lenses, to form metal detectable eyewear. Disclosed lens carriers can mechanically hold the at least one lens. The at least one lens can be releasably held by the lens carrier or can be permanently held by the lens carrier. A disclosed lens carrier can be combined with one lens, or two lenses for example. The metal detectable eyewear can be glasses, goggles, or a safety shield, for example, as illustrated above, or any other eyewear.

Disclosed lens carriers can be combined with generally utilized safety lenses, prescription lenses, or both. Disclosed lens carries can also be combined with metal detectable lenses. Exemplary metal detectable lenses can be found in the commonly assigned United States patent application entitled "METAL DETECTABLE LENS", having Donald Seeto as an inventor, filed on even date herewith Ser. No. 12/764,122.

Methods of detecting at least a portion of metal detectable safety eyewear are also disclosed herein. One such exemplary method is depicted in FIG. 6. The first step in such a method, step 62, is providing metal detectable eyewear. The step of providing metal detectable eyewear can include providing any metal detectable eyewear that includes a disclosed lens carrier. The step of providing can be accomplished for example by manufacturing, purchasing, or simply providing the eyewear to a user. In embodiments, the metal detectable eyewear can also optionally include a metal detectable lens or lenses.

The next step, step 64, includes passing at least a portion of the lens carrier through a metal detector. The metal detector can include any type of metal detector that is capable of detecting the portion of the lens carrier. In some embodiments, the metal detector can include those that are commonly used in the food industry, or other manufacturing industries. Metal detectors that can be utilized can be configured within a larger piece of manufacturing equipment or can be freestanding.

The next step, step 66, includes detecting the portion of the lens carrier. The portion of the lens carrier can be detected by detecting a portion of the metal particulate in the lens carrier. The metal detector, as discussed above, generally functions to detect the portion of the lens carrier. In embodiments, the portion of the lens carrier detected can be as small as about 0.08 g.

Thus, embodiments of metal detectable lens carriers are disclosed. One skilled in the art will appreciate that the present disclosure can be practiced with embodiments other than those disclosed. The disclosed embodiments are presented for purposes of illustration and not limitation, and the present disclosure is limited only by the claims that follow.

What is claimed is:

1. A metal detectable lens carrier comprising:
a polymeric material; and
a metal particulate dispersed throughout the polymeric material;
wherein the metal detectable lens carrier is configured to hold one or more lenses.

2. The metal detectable lens carrier according to claim 1, wherein a portion of the carrier as small as 0.08 g can be detected by a metal detector calibrated to detect a 1.5 mm diameter steel ball.

3. The metal detectable lens carrier according to claim 1, wherein the polymeric material comprises polyamide, polyolefin, polycarbonate, or a combination thereof.

4. The metal detectable lens carrier according to claim 1, wherein the polymeric material comprises Nylon 6-6.

5. The metal detectable lens carrier according to claim 1, wherein the metal particulate comprises silver (Ag), copper (Cu), gold (Au), aluminum (Al), beryllium (Be), iridium (Ir), tungsten (W), molybdenum (Mo), cobalt (Co), zinc (Zn), nickel (Ni), chromium (Cr), titanium (Ti), or a combination thereof.

6. The metal detectable lens carrier according to claim 1, wherein the metal particulate comprises metal fiber.

7. The metal detectable lens carrier according to claim 1, wherein the lens carrier can withstand a ¼" steel ball projected thereon at a velocity of about 150 feet/second.

8. The metal detectable lens carrier according to claim 1, wherein an amount (by weight) of metal particulate to polymeric material can be from about 5% to about 50% of total weight of a lens carrier portion or an entire lens carrier.

9. The metal detectable lens carrier according to claim 1, wherein the lens carrier comprises a frame and temples.

10. The metal detectable lens carrier according to claim 9, wherein the lens carrier further comprises one or more nosepieces.

11. The metal detectable lens carrier according to claim 1, wherein the lens carrier consists essentially of the polymeric material and the metal particulate.

12. Metal detectable eyewear comprising:
at least one optical lens; and
a lens carrier configured to hold the at least one optical lens, wherein the lens carrier comprises:
a polymeric material; and
a metal particulate dispersed throughout the polymeric material.

13. The metal detectable eyewear according to claim 12 further comprising two lenses.

14. The metal detectable eyewear according to claim 12, wherein the lens carrier comprises a frame and temples.

15. The metal detectable eyewear according to claim 14, wherein the lens carrier further comprises one or more nosepieces.

16. The metal detectable eyewear according to claim 12, wherein the metal detectable eyewear is glasses, goggles, or shield.

17. The metal detectable eyewear according to claim 12, wherein the at least one optical lens is metal detectable.

18. A method of detecting at least a portion of a metal detectable eyewear, the method comprising:

providing metal detectable eyewear, the metal detectable eyewear comprising:

at least one optical lens; and a lens carrier configured to hold the at least one optical lens, wherein the lens carrier comprises:

a polymeric material; and a metal particulate dispersed throughout the polymeric material;

passing at least a portion of the lens carrier through a metal detector;

detecting at least the portion of the metal detectable eyewear by detecting the metal particulates in the lens carrier through use of the metal detector.

19. The method according to claim 18, wherein the portion of the lens carrier can be as small as about 0.08 g and still be detected.

20. The method according to claim 18, wherein the metal detectable eyewear can be detected by detecting at least a portion of the at least one optical lens.

* * * * *